United States Patent [19]

Kosakewich

[11] Patent Number: 5,327,608
[45] Date of Patent: Jul. 12, 1994

[54] MOVING BRISTLE BRUSH

[76] Inventor: Michael P. Kosakewich, 2500 Newport Dr., Fort Collins, Colo. 80526

[21] Appl. No.: 992,547

[22] Filed: Dec. 17, 1992

[51] Int. Cl.⁵ .................... A61C 15/00; A46B 13/02
[52] U.S. Cl. .................... 15/22.1; 15/167.1; 15/172
[58] Field of Search .......... 15/22.1, 167.1, 167.2, 15/201–203, 160, 172; 128/62 A; 433/216

[56] References Cited

U.S. PATENT DOCUMENTS

| 2,111,880 | 3/1938 | Waters | 15/172 |
| 2,244,098 | 6/1941 | Busick | 15/172 |
| 4,467,491 | 8/1984 | Dekker | 15/203 |
| 4,795,347 | 1/1989 | Maurer | 15/167.2 |

Primary Examiner—Edward L. Roberts
Attorney, Agent, or Firm—Fields, Lewis, Pittenger & Rost

[57] ABSTRACT

A brush has bristles that tilt laterally out in a first position and tilt laterally in in a second position and are moved back and forth between the two positions to provide a brushing action. The bristles shown are mounted on a flexible membrane that is in an outwardly extending convex configuration to dispose the bristles in the first position and in an inwardly extending convex configuration to dispose the bristles in the second position. A bladder filled with a non-compressible fluid and an electric solenoid are used to move the flexible membrane between the two positions in a continuous cycle.

10 Claims, 1 Drawing Sheet

MOVING BRISTLE BRUSH

TECHNICAL FIELD

This invention relates to brushes and more particularly to a novel moving bristle brush that is particularly suitable for brushing teeth.

BACKGROUND ART

Numerous attempts have been made to improve the brushing action of a brush and particularly for the brushing of teeth.

DISCLOSURE OF THE INVENTION

A brush having bristles tilted laterally out in a first position and tilted laterally in in a second position with actuating means to move the bristles back and forth between the two positions in a continuous cycle to provide a brushing action that is generally transverse to brush movement longitudinally of the brush. The bristles are mounted in a flexible membrane that responds to the pressurization of a bladder. The bladder is responsive to an electric solenoid.

BRIEF DESCRIPTION OF THE DRAWINGS

Details of this invention are described in connection with the accompanying drawings which like parts bear similar reference numerals in which.

DETAILED DESCRIPTION

Figure 1:
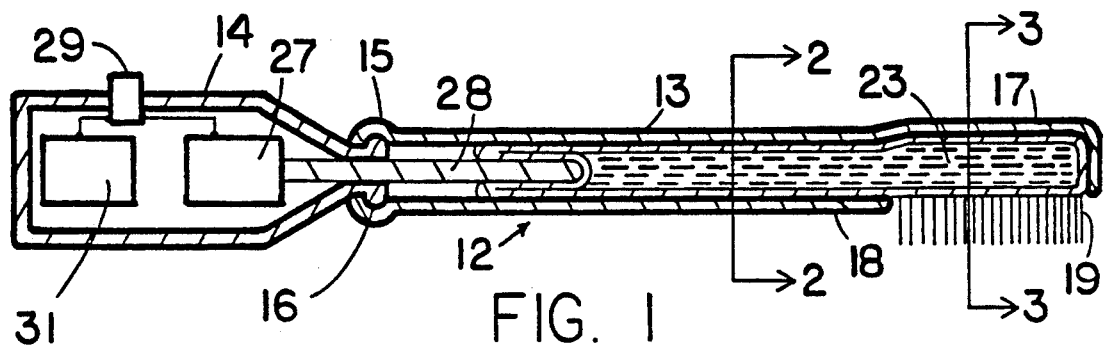
FIG. 1 is a longitudinal cross sectional view of a brush embodying features of the present invention with the drive rod extended and the bristles in a tilted laterally out position and with the drive and control shown in schematic form inside the handle.
Figure 2:
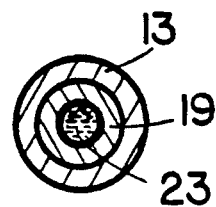
FIG. 2 is a sectional view taken along line 2—2 of FIG. 1.

Referring now to the drawings there is shown a brush 12 that is particularly suitable for use as a toothbrush which in general is made with a rigid front housing section 13 and a rigid rear handle section 14 that releasably fasten to one another at a snap-fit joint. This joint includes a female coupling portion 15 on the rear end of the housing section 13 and a male coupling portion 16 on the front end of the handle section 14. The male coupling portion 16 is in the form of an annular ring-type enlargement and the female coupling portion 15 is a recessed area formed on the inside of the male portion that is complementary in shape with that of the annular ring-type enlargement. The front housing section 13 has a forward head portion 17 and a rear elongated neck portion 18. Bristles 19 are shown as mounted inside the head portion 17 on a flexible membrane 21 which is shown as part of an elongated tubular bladder 22 contained inside the front head portion 17 and extending rearwardly along the neck portion 18. The bristles protrude outwardly from an opening in the head portion 17. The bladder has a closed inner chamber that contains a non-compressible fluid 23. The rear end portion of the bladder has a rounded end portion 24 so that it resembles a glass test tube. The diameter of the drive rod 28 is less than the diameter of the tubular bladder 22 in the neck section so that the drive rod can pass inside the bladder as seen in FIG. 1. It is understood that the flexible membrane 21 could be made separate from the bladder and simply mounted on the bladder.

The bristles 19 are supported on the membrane 21 of the bladder with the flexible membrane 21 being arranged along an outwardly convex curve in what is herein referred to as the first position so as to dispose the bristles 19 tilted laterally out with respect to a vertical center line of the membrane designated 25. The bladder will move to a second position wherein the membrane 21 is inwardly concave in the second position and the bristles tilt laterally in with respect to the vertical center line 25 of the membrane. The bristles 19 extend transverse or orthagonal to the exterior surface of the membrane 21. The angle that the bristles tilt out and in from the vertical center line is relatively small as on the order of eight degrees and may vary as on the order of about three degrees to fifteen degrees.

Figure 3:
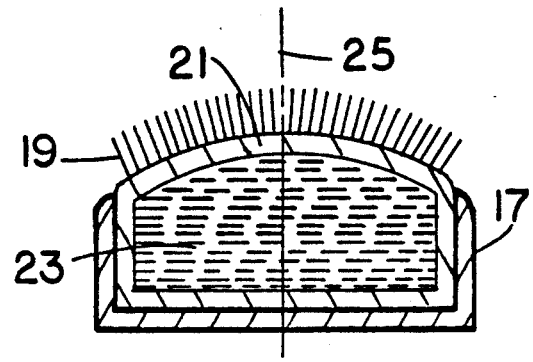
FIG. 3 is a sectional view taken along line 3—3 of FIG. 1.
Figure 5:
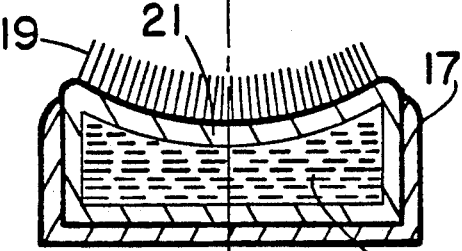
FIG. 5 is the same sectional view as FIG. 3 with the drive rod retracted and the bristles in a tilted laterally in position.
Figure 4:
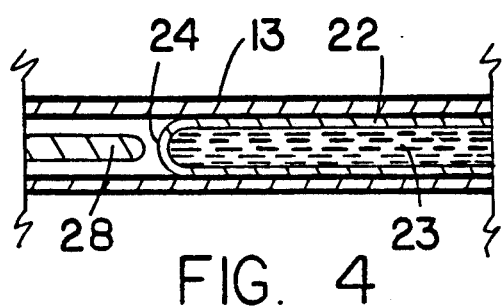
FIG. 4 is a fragmentary sectional view showing the drive rod retracted and the bladder in a normal non-deformed position.

The drive for moving the bristles 19 between the first and second positions includes a solenoid 27 having the main body thereof disposed in the handle section 14 having a reciprocating rod 28 that extends through the handle section 14 and into the front housing section 13. The reciprocating rod 28 as shown in FIG. 1 is extended and projects a distance into the inside of the bladder. This deforms the bladder to decrease the volume of the chamber and increases the pressure to cause the membrane 21 to move to the first position shown in FIGS. 1 and 3 which locates the bristles in the outwardly tilted or inclined position. When the rod 28 is moved by the solenoid 27 to the retracted position then the bladder is in a normal non-deformed position as is seen in FIG. 4. The flexible membrane 21 is formed with a memory to automatically return to the inwardly concave position FIG. 5 when the bladder is not deformed (FIG. 4) and the pressure is removed. It is understood that the portion of the bladder inside the head portion and with the membrane may be constructed as one bladder and the tubular bladder inside the handle section as a separate bladder and the two connected by a flow line. It is further understood that the membrane may be a part separated from the bladder and moved by pressurizing and depressurizing the bladder.

As shown in schematic form in FIG. 1 in the handle section 14 there is an electric switch 29 electrically connected by wires between the solenoid 27 and the electric power supply 31 which may be, for example, a D.C. battery. Once the switch is actuated to connect the electric power from supply 31 to the solenoid 27, the solenoid will reciprocate in a continuous cycle causing the bristles 19 to move or oscillate in a back and forth action to provide a lateral brushing action that is generally transverse to the housing and handle sections and the longitudinal movement thereof during the use of the brush. It is understood that other drive means can be used for moving the membrane between the two positions. In place of the fluid filled bladder other mechanical arrangements connected directly to the membrane could be used to cause the membrane to move and other reciprocating drives such as a rack gear and pinion may be used.

Although the present invention has been described with a certain degree of particularity, it is understood that the present disclosure has been made by way of example and that changes in details of structure may be made without departing from the spirit thereof.

What is claimed is:

1. A brush comprising:
a head portion having bristle support means on which a plurality of bristles are mounted and project transversely away from an exterior surface of said support means, said support means having a convex contour in a first configuration that positions said bristles so as to tilt laterally out with respect to a vertical center line of said support means at a first bristle position, said support means having a concave contour in a second configuration that positions said bristles so as to tilt laterally in with respect to a vertical center line of said support means at a second bristle position and means operating on said support means for moving said support means between said first and second configurations and said bristles back and forth between said first and second bristle positions to provide a brushing action by the movement of said bristles.

2. A brush as set forth in claim 1 wherein said bristle support means is in the form of a flexible membrane.

3. A brush as set forth in claim 1 wherein said means for moving includes a bladder having a closed inner chamber containing a non-compressible fluid, said bladder being operatively associated with said bristle support means and a reciprocal drive having a drive rod with a retracted position and an extended position, said drive rod moving against said bladder to cause said bristle support means to move said support means between said configurations.

4. A brush as set forth in claim 3, wherein said bladder has a tubular, rounded end portion opposite said bristle support means with said drive rod moving against said end section and into said tubular portion in the extended position to reduce the volume of said chamber and pressurize said chamber.

5. A brush as set forth in claim 3 wherein said means for moving is in the form of an electric solenoid with said drive rod arranged so that upon electrical energization the drive rod reciprocates back and forth in a reciprocating movement and a switch is connected between said solenoid and a power supply to selectively turn said solenoid either on or off.

6. A brush as set forth in claim 1 wherein the angle the bristles tilt out and in is on the order of about three degrees to about fifteen degrees, 7. A brush assembly comprising:
a front housing section and a rear handle section releasably fastened to said front housing section, said front housing section having a head portion and an elongated neck portion,
bristles projecting out from an opening in said head portion,
a bladder with a closed chamber containing a fluid disposed in said front housing section, said bristles being mounted to a bristle support portion of said bladder and project transversely away from an exterior surface of said bristle support portion, said bristle support portion having a convex contour in a first configuration that positions said bristles so as to move between a first bristle position having the bristles tilt laterally out with respect to a vertical center line of said bristle support portion, said support portion having a concave contour in a second configuration that positions said bristles so as to tilt laterally in with respect to a vertical center line of said support means at a second bristle position,
a drive operating on said bristle support portion for moving bristle support portion between said first and second configurations and said bristles between said first and second bristle positions, said drive including a solenoid in said handle section having a reciprocating drum rod that engages an end portion of said bladder and moves inside said bladder to deform said bladder and decrease the volume of the chamber when extended and out of said bladder in the retracted position in a continuous reciprocating cycle when said solenoid is actuated, and
means to selectively control the actuation of said solenoid.

8. A brush assembly as set forth in claim 7 wherein said front housing section and said rear handle section have associated male and female coupling portions that snap-fit together.

9. A brush assembly as set forth in claim 7 wherein the diameter of said drive rod is sufficiently smaller than the diameter of said bladder to enable said drive rod to decrease the volume of said chamber in said bladder.

10. A toothbrush comprising:
a head portion and a handle section having bristle support means on which a plurality of bristles are mounted and project transversely away from an exterior surface of said support means, said support means having a convex contour in a first configuration that positions said bristles so as to tilt laterally out with respect to a vertical center line of said support means at a first bristle position, said support means having a concave contour in a second configuration that positions said bristles to tilt laterally in with respect to a vertical center line of said support means at a second bristle position and means operating on said support means for moving said support means between said first and second configurations and said bristles back and forth between said first and second bristle positions to provide a brushing action by the movement of said bristles.

* * * * *